United States Patent
Eaton

(10) Patent No.: US 9,242,019 B2
(45) Date of Patent: Jan. 26, 2016

(54) UV PIPE

(71) Applicant: Mark F Eaton, Austin, TX (US)

(72) Inventor: Mark F Eaton, Austin, TX (US)

(73) Assignee: STELLARRAY, INCORPORATED, Austin, TX (US)

(*) Notice: Subject to any disclaimer, the term of this patent is extended or adjusted under 35 U.S.C. 154(b) by 0 days.

(21) Appl. No.: 14/209,494

(22) Filed: Mar. 13, 2014

(65) Prior Publication Data

US 2015/0262780 A1 Sep. 17, 2015

(51) Int. Cl.
*H01J 63/00* (2006.01)
*A61L 2/10* (2006.01)
*A61L 9/20* (2006.01)
*H01J 63/02* (2006.01)

(52) U.S. Cl.
CPC . *A61L 2/10* (2013.01); *A61L 9/205* (2013.01); *H01J 63/02* (2013.01)

(58) Field of Classification Search
CPC .............. H01J 5/125; H01J 5/12; A61L 2/10
USPC ........................................................ 313/636
See application file for complete search history.

(56) References Cited

U.S. PATENT DOCUMENTS

| | | | |
|---|---|---|---|
| 1,724,298 A | 8/1929 | Miller | |
| 3,375,391 A | 3/1968 | Day | |
| 3,941,715 A | 3/1976 | Shidlovsky | |
| 4,014,813 A * | 3/1977 | Shidlovsky | ............. 252/301.4 P |
| 4,274,028 A | 6/1981 | Frame | |
| 5,045,754 A | 9/1991 | Clerc | |
| 5,341,065 A | 8/1994 | Uemura | |
| 6,525,485 B2 | 2/2003 | Kasano | |
| 6,624,566 B2 | 9/2003 | Uemura | |
| 7,300,634 B2 | 11/2007 | Yaniv | |
| 8,632,728 B2 | 1/2014 | Shim | |
| 2008/0061667 A1 * | 3/2008 | Gaertner et al. | ............. 313/113 |

FOREIGN PATENT DOCUMENTS

CN          202920686          5/2013

OTHER PUBLICATIONS

Williams et al, "Laser action in strongly scattering rare-earth-metal-doped dielectric nanophosphors," Phys. Rev. A65. 013807(2001).
Li, et al, "Continuous-wave ultraviolet laser action in strongly scattering Nd-doped alumina," Opt. Lett. 27. 394 (2002).

* cited by examiner

*Primary Examiner* — Anne Hines

(57) ABSTRACT

A pipe source of UV flux has an inner pipe made of UV transmissive material and coated on its outer surface with a UV emitting phosphor. An outer pipe has a cathode array disposed on or near its inner surface, such as an array of thermionic filament cathodes mounted longitudinally or transverse to the length of the pipe, cold cathode arrays formed on the inner surface of the pipe or cold cathode arrays formed on separate substrates which are then attached to the inner surface of the outer pipe. The ends of this two-pipe assembly are hermetically sealed with flanges or end plates at either end of the pipe and evacuated to a pressure below $1 \times 10^{-3}$ Torr. Internal spacing rings may be used to provide additional separation between the inner and out pipes. Current from the cathode arrays is accelerated by an anode voltage to strike the UV phosphors when then emit UV light flux which illuminates the inside of the pipe and the fluid material flowing through the inner pipe.

3 Claims, 2 Drawing Sheets

UV PIPE

STATEMENT REGARDING FEDERALLY FUNDED RESEARCH AND DEVELOPMENT

Parts of this invention were made with U.S. Government support under National Science Foundation Grant No. 1013887. The Government has certain rights in the invention.

PRIORITY DATA

Provisional application No. 61/784,866, filed on Mar. 14, 2013.

BACKGROUND OF THE INVENTION

This invention provides a pipe source of ultraviolet radiation which uses cathode arrays to emit electron beam current to excite cathodoluminescent phosphors emitting in the ultraviolet (UV) portion of the electromagnetic spectrum (100 to 400 nanometers in wavelength). The phosphors can be selected to emit in any part or parts of the UV bands. UV-A and UV-B phosphors can be used for in various industrial applications. UV-C phosphors can be incorporated in the pipe sources of this invention for applications such as water or air purification, through either direct or photocatalytic sterilization of contaminants. Fluids such as air or water flow through the pipe and are evenly irradiated with UV flux. In certain aspects of this invention, the ultraviolet phosphors can be mixed together to provide a desired multi-spectral output. In other aspects, different wavelength phosphors can be deposited on different parts of the phosphor pipe, so that the different spectra can be selectively addressed for light emission.

Most UV sources now used are fluorescent gas discharge tubes or lamps, most commonly with a low or medium pressure mercury vapor medium for the gas discharge. These sources have a number of limitations, including the hazard of the mercury in the tubes, risks of breakage, narrow spectral range, low power efficiency, especially in the case of medium pressure mercury vapor tubes, sensitivity to temperature variations, heat generation, and difficulties in cleaning and maintenance in some applications. UV light emitting diodes (LEDs) have been developed more recently. These have low power efficiency below about 365 nm in wavelength and also suffer from "droop", a phenomenon in which power efficiency drops further as power output is increased. LEDs are also made on compound semiconductor wafers such as AlGaN, so they are expensive to begin with and then have to be diced and assembled for larger area applications, which adds further to the cost of a wide area UV source.

U.S. Pat. Nos. 4,274,028 and 7,300,634 disclose flat panel sources of cathodoluminescent UV flux in which the phosphors are excited by electron beam current emitted from cold cathode films or cold cathode arrays. For sterilization or other treatment of fluids such as air or water, a pipe source of UV flux would provide increased efficiency, safety and convenience.

OBJECTS AND ADVANTAGES OF THE INVENTION

It is an object of this invention to provide an inexpensive, power-efficient source of UV flux in a convenient pipe format which can easily be scaled both in terms of physical size and power output. Other objects of the invention are to provide variation of the ultraviolet emission bands both between different sections of the pipe and in other cases within the same pipe by the use of different phosphor materials. A further object of this invention is to provide a safe source of UV flux in which the flux is completely shielded by the source itself. Yet another object of the invention is to provide a UV source in which powder laser phosphors are used instead of cathodoluminescent phosphors to further increase the power efficiency of the source.

SUMMARY OF THE INVENTION

The invention disclosed herein provides a pipe source of UV flux in which an inner pipe made of UV transmissive material is coated on its outer surface with a UV emitting phosphor. A conductive layer is formed under or over this phosphor layer which is UV-transmissive if under the layer and UV reflective if over the phosphor layer. An outer pipe has a cathode array disposed on or near its inner surface, such as an array of thermionic filament cathodes mounted longitudinally or transverse to the length of the pipe, cold cathode arrays formed on the inner surface of the pipe or cold cathode arrays formed on separate substrates which are then attached to the inner surface of the outer pipe. The ends of this two-pipe assembly are hermetically sealed with flanges or end plates at either end of the pipe and the space between the inner and out pipes is evacuated to a pressure below $1 \times 10^{-3}$ Torn Internal spacing rings, flanges or struts may be used to provide additional mechanical separation and support between the inner and outer pipes. Current from the cathode arrays is accelerated by an anode voltage to strike the UV phosphors which then emit UV flux which illuminates the inside of the pipe and the fluid material flowing through the inner pipe.

DETAILED DESCRIPTION OF THE INVENTION

Although the following detailed description delineates specific attributes of the invention and describes specific designs and fabrication procedures, those skilled in the arts of electronics or radiation source production will realize that many variations and alterations in the fabrication details and the basic structures are possible without departing from the generality of the processes and structures. The most general attributes of the invention relate to the generation of UV flux from phosphors coated on wide, UV transmissive anode pipe and excited by electron beam current(s) from one or more thermionic cathode filament arrays mounted in frames on or near a cathode pipe opposite the anode pipe and separated from the inner pipe by a vacuum space.

Figure 1:
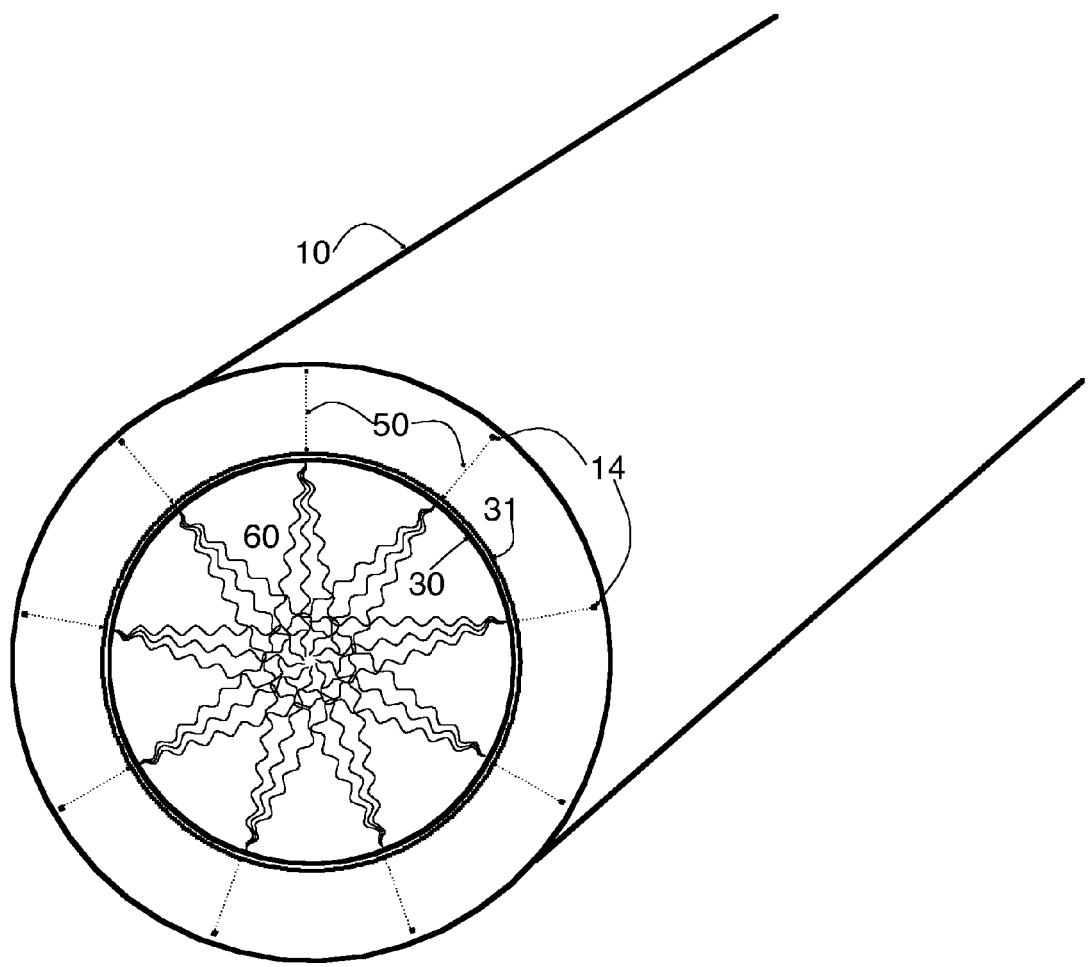
FIG. 1 shows the UV pipe of this invention in which an array of cathodes formed around the inner surface of an outer pipe emits electron beam current towards a phosphor layer on the outer surface of a UV transmissive inner pipe to irradiate material flowing through the inner pipe.

The basic construction of the vacuum UV pipe of the present invention is shown in FIG. 1. An inner pipe 30 made of UV transmissive material such as quartz or UV transmissive borosilicate glass is coated on its outer surface with UV emitting phosphor 31. This serves as the anode of the source. A conductive layer may be formed under or over this phosphor layer which is UV-transmissive if under the layer and UV reflective, such as aluminum, if over the phosphor layer. Outer cathode pipe 10 has an array of cathodes 14 disposed on or near its inner surface, such as an array of thermionic metal filament cathodes mounted longitudinally or transverse to the length of the pipe, cold cathode arrays formed on the inner surface of the pipe or cold cathode arrays formed on separate substrates which are then attached to the inner surface of the outer pipe. FIG. 1 depicts cross sections of a longitudinal array of filament cathodes. The ends of this two-pipe assembly are then sealed with flanges and evacuated to a pressure below $1 \times 10^-$ Torr. Vacuum pump-out ports and electrical connections to the cathode arrays, anode and optional grid or gate electrodes may made through these flanges. Internal spacing rings, flanges or struts may be used to provide additional mechanical separation and support between the inner and outer pipes. Current from the cathode arrays is accelerated by an anode voltage to strike the UV phosphors when then emit UV flux which illuminates the inside of the pipe and the fluid material flowing through the inner pipe. While the source is shown as a round pipe in FIG. 1, other shapes may also be used, such as square tubes.

The electron beam current may be directly accelerated towards the anode pipe by an acceleration voltage between the anode pipe and the filaments, or between the anode and a metallic ground plane (thin film of conductive material) formed on the inner surface of the cathode pipe. Alternatively, a mesh grid with substantial open area (preferably over 90% open) can be operated with a grid or gating voltage to allow the electrons to pass through the grid and then be accelerated toward the anode. This grid electrode has the additional function of more evenly distributing the electron beam current over the anode pipe. The anode pipe is made of UV transmissive material, such as quartz or a borosilicate glass with high UV transmission. The phosphor layer deposited on the anode pipe emits UV light flux when struck by the accelerating electron beam current. The UV flux passes through the anode pipe and into the fluids in the pipe. The phosphor layer itself may provide the electrical connection for the anode accelerating voltage. A transparent conductive layer may be disposed between the phosphor layer and the anode pipe to provide this electrical connection. Alternatively, for UV phosphors which emit light upon impact of higher energy electrons, generally above 2 kV, a thin layer of UV reflective material such as aluminum may be deposited over the phosphor layer with the opposite surface of this metal layer facing the vacuum of the source. These conductive layers are deposited by sputtering, thermal evaporation, electroplating or other methods known in the art of thin film deposition. Higher energy electrons will penetrate this metal layer and excite the phosphors. The metal layer will suppress outgassing from the phosphors into the vacuum and reflect UV light emitted in the direction of the vacuum and cathode array back out the anode pipe, so as to increase the power efficiency of the source.

The thickness of the inner anode pipe 30 is chosen to allow as much of the UV flux out of the source as possible while at the same time providing sufficient mechanical strength to withstand atmospheric load. An exemplary thickness of quartz used as the anode pipe is between 1 mm and 5 mm. The cathode pipe can be of any thickness needed for mechanical strength under atmospheric load. The cathode pipe may also be made of metals or other materials with high thermal conductivity so as to allow cooling of the source from outer surface of the cathode pipe. If the cathode pipe is made of quartz, it may be coated with a UV blocking material. Since the cathode pipe will not allow UV flux to pass outside the source, the source may be operated safely, with no need for extra shielding of personnel operating the source. External cooling structures such as heat sinking materials, air cooling fins or fluid cooling structures may be added to the outside of the cathode pipe to allow the source to operate at high power levels. A further outer pipe may also be used to run coolant through for the cathode pipe, to provide UV shielding, or to provide electrical insulation when the anode pipe is at ground and the cathode pipe is at high voltage. Electrical insulation such as insulating gas, potting compound or vacuum can be used in the space between the cathode pipe and this further outer pipe.

Figure 2:
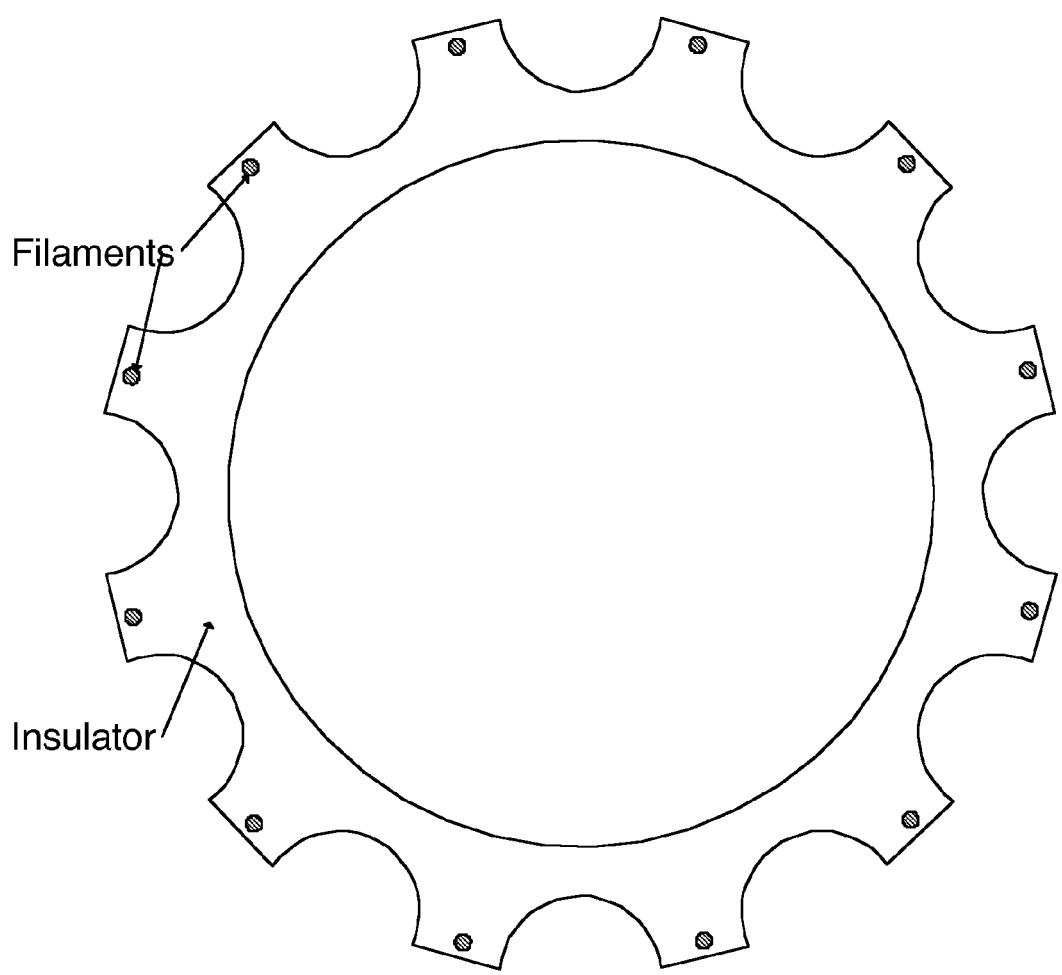
FIG. 2 shows one design of a spacing ring that can be used to maintain the separation between the inner and outer pipes. In this design connections are provided for filament cathodes. Other designed can provide for attachment of cold cathode substrates, grid electrodes, getters and other components of the sources.

The end walls or flanges form the other parts of the vacuum envelope of the source. These are preferably made of an insulating material such as glass or ceramic and may be made of the same material, such as quartz or borosilicate glass, as the anode pipe. Metal flanges may also be used, provided they have an inner section of insulating material between the metal contacts to the anode and cathode pipes. Internal support spacers, such as shown in FIG. 2, may be disposed between the cathode and anode pipes to provide separation between the two pipes and mechanical support under vacuum load for longer pipes. They may also be used to hold the cathode arrays in place. As shown in FIG. 2, for example, filament cathodes may be attached directly to these support spacers, or the filaments may be run through holes in them. The support spacers are preferably coated with a charge bleed layer made of a very thin film of metal or semiconductor material so as to drain any charge built up from stray electrons or ions produced in operation and prevent electrical flashover inside the vacuum package. These structural components—anode pipe, cathode pipe, side walls and internal support bars—are preferably chosen to have similar coefficients of thermal expansion so as to reduce stresses in the vacuum envelope as the source is being operated.

Scaling of the size of the source may be done in several ways. First, the pipe diameters may be increased. Common sizes for water or air flow are exemplary. Second, the length of the pipe may be increased. Third, bolt holes or other connections can be provided in the pipe end flanges and they can be joined together for as long as needed. They can also be run in parallel.

The accelerating voltage is provided by an external power supply connected to the ground plane, filaments or grid on one side and the phosphor layer, transparent conductive layer or metal covering layer on the anode side through electrical connections running through the vacuum package of the source. The accelerating voltage is chosen to fit the electron energy level needed for efficient excitation of the phosphors. With some exemplary UV-C phosphors this is between 5 kV and 20 kV. For other phosphors, much lower voltages under 1 kV are most efficient. The source may be operated in DC mode, with a constant stream of electron beam current supplied to the anode, or it may be pulsed so as to prolong phosphor life or increase the intensity of the UV flux.

The power level of the source is chosen based on the efficiency of the phosphor and flux intensity needed for the application. In an exemplary application of UV-C pipes used for sterilization of air or water, the desired flux intensity is about 15 mW/cm$^2$. Some available UV-C phosphors operate at peak conversion efficiency of about 10% at a voltage of about 8 kV. In this case, about 0.02 mA/cm$^2$ is required from the cathode arrays, to deliver about 6 W of UV-C flux from the pipe with 60 W of input power.

Numerous types of cathode arrays can be used to supply the electron beam current in the disclosed UV pipe source, including thermal filament arrays, thin film thermal filament cathodes, photocathodes and cold cathode arrays. Cold cathodes such as those formed from carbon nanotubes may also be grown directly on the inner surface of the cathode pipe.

Filament cathodes may be disposed on the inner surface of the cathode pipe longitudinally (along the long axis of the pipe), transverse (around the inner circumference of the pipe, or in any other suitable configuration. They may be held in preformed frames, attached to the inner surface of the cathode pipe, attached to support structures on the inner surface of the cathode pipe, attached to the end or attached to or through internal support spacers such as those shown in FIG. 2. Preformed frames are preferably made of stamped metal but can also be made of an insulating material provided that conductive leads are disposed in the frame ends to connect to the filaments. Insulating frame sides may be provided to keep the frame rigid. Leaf, coil or other springs may be provided on at least one of the frame ends, or on the end plates, flanges, internal support spacers, or inner cathode pipe walls to keep the filaments taut and prevent sagging as the filaments expand and contract under heating.

Filament sagging is to be avoided since too much of the current will be provided from the middle of the filament, which will shorten cathode lifetime. When a grid is used, the filament can short to the grid if it sags too much. An exemplary length of the filaments in the disclosed source is from 10 mm to 200 mm. The width can be any width desired. By holding the filaments in frames, the size of the source can be scaled to as large as desired simply by adding more frames. The frames are mechanically attached to the cathode pipe, side walls or support spacers by clips, welding, frit adhesion, connecting rods or any other suitable mechanical means. The filaments may be made of any thermionic emitting material. Exemplary materials include W wires, thoriated (2.5%) W (Th—W) wires, low temperature Barium-coated W (Ba-coated W), and Triple Carbonate (Ba—Sr—Ca)$CO_3$ coated W wires.

Cold cathode arrays may also be used to supply the electron beam current of the source. Any type of cold cathode—flat, surface conduction emitter, vertical tips arrays of metal semiconductor or carbon, carbon nanotubes, or lateral edge emitter or lateral edge emitting tips—can be formed and tested on separate substrates which are then cut into a suitable shape and affixed on to or near the inner surface of the cathode pipe. A convenient attachment scheme is to fit, weld, frit seal or otherwise affix long rectangular substrates with cold cathode arrays to internal support structures such as that shown in FIG. 2. The long axis of the substrates can be parallel to the long axis of the pipe. As an example, a cathode with an inside diameter of 10 cm could accommodate about 31 substrates with a width of 1 cm, with the substrates confirming closely to the circumference of the cathode pipe. Cold cathode arrays may be provided with integrated grid or gating structures for lower voltage driving of the current, and with resistors to improve cathode stability and lifetimes.

Evaporable or non-evaporable getters may be conveniently placed on cathode filament frames, on the front or back of cold cathode substrates, on internal support spacers, elsewhere on cathode support structures, or on the inner surfaces of the cathode or anode pipes. These are activated after vacuum sealing of the source to absorb gases released inside the source during operation, thereby maintaining the vacuum of the source.

Any cathodoluminescent or powder laser phosphor or combination of phosphors, including nanoparticle phosphors, can be used in the disclosed source, which can therefore emit light in a number of spectral regions. A number of phosphors exist in the prior art which emit UV-C in response to cathodoluminescent excitation. U.S. Pat. No. 3,941,715 discloses a zirconium pyrophosphate phosphor, while U.S. Pat. No. 4,014,813 discloses a hafnium pyrophosphate phosphor and U.S. Pat. No. 4,024,069 discloses a yttrium tantalate phosphor, all of which emit UV-C radiation in response to excitation by an electron beam. In addition, lanthanum pyrophosphates developed primarily for fluorescent tubes are also known to emit UV-C in response to cathodoluminescent excitation. More recently, powder laser phosphors have been developed which emit in the UV-C region (Williams et al, "Laser action in strongly scattering rare-earth-metal-doped dielectric nanophosphors," Phys. Rev. A65, 013807(2001); and Li, et al, "Continuous-wave ultraviolet laser action in strongly scattering Nd-doped alumina," Opt. Lett. 27, 394 (2002)). Other phosphors can be used for UV-A and UV-B emission. These include phosphors, typically based upon borate, fluoroborate and silicate compounds, for UV-A lamp applications such as tanning beds, black lights and medical procedures. These are generally now excited by gas discharge but may also perform under cathodoluminescence. Other phosphors may be chosen for high cathodoluminescent efficiency, such as sulfur-containing phosphors. These include ZnS based phosphors developed for CRT applications, and Pb activated CaS. Other S containing phosphors, such as the Ca/Ba sulfates activated with Eu or Ce may also be used. For example, $CaSO_4$:Eu has a relatively narrow emission peaking at 388 nm while $CaSO_4$:Ce has a broad emission peak extending from 300 to 345 nm.

Powder phosphors may be deposited on the outer surface of the anode pipe by settling with or without phosphor particle binders, by electrophoretic methods, screen printing, pressing, or by ink jet methods. Thin-film phosphors may also be used, in which case subsequent doping of the layer may be used to tune the spectral distribution of the flux. Scintillating ceramic phosphor layers are another exemplary material for the phosphor layer. Powder laser phosphors may also be used, with the electron beam current operated to pump the laser materials.

A current gating grid may be provided between the cathode array and anode, but closer to the cathode array to modulate the electron beam current and to provide more even distribution of the beam current over the anode pipe. The grid is preferably made from a thin metal foil etched to provide substantial open area. A suitable grid voltage will extract electrons emitted by the cathodes and direct them towards the anode. As a rule of thumb, the grid voltage is generally most effective at about 100 V per mm of separation between the grid and the cathodes. The grid may be formed as a continuous foil covering all or part of the area of the source, or it may be formed in sections corresponding to the area of the cathode frame. It can be secured beneath the cathodes by a number of methods, including mechanical attachment to internal support spacers or directly to cathode frames or substrates.

The disclosed UV pipe source may be evacuated and sealed by a number of methods. The distance between the cathode pipe and the anode pipe may be set according to the electrical potential used between cathode and anode. The distance should be sufficiently large to prevent arcing or other vacuum breakdown between cathode at anode at the chosen voltage. It should also be large enough to prevent external breakdown between conductive components such as feedthroughs on the external side of the source. An exemplary distance for a 10 keV potential is 2-10 millimeters. The cathode pipe, anode pipe and end plates or flanges may be joined with frit glass sealing techniques common in the vacuum tube and flat panel display industries. Quartz pipes and end pieces may be sealed through frit seals in some cases, or they may be flame sealed. Another method for sealing is to provide a compressable solder on the ends of the cathode and anode pipes. The end plates or flanges may be provided with a groove or cavity to accept this solder. The end plate or flanges are then pressed together so as to press the solder into place as a hermetic or near hermetic seal. Epoxy may be applied outside this solder seal, or mechanical clips, braces or bolts may be applied, to hold the assembly together. In an exemplary flange seal, metal end rings are attached to the end of the cathode and anode pipes by brazing, graded seals or other methods known in the art. Metal end flanges, with insulating material between the inner circumference of the flange, corresponding to the circumference of the anode pipe, and the other circumference of the flange, corresponding to the circumference of the cathode pipe, are provided with solder seal, conflat or other types of hermetic sealing structures. The metal end flanges are pressed and held into place using clips, bolts or other methods known in the art of vacuum sealing. Alternative sealing methods include O-ring seals of high-temperature materials such as Viton™ and mechanical clamping supports, vacuum-compatible epoxies or silica-based sealants. Electrical connection and getter activation feedthroughs may be provided through end plates or flanges or through the cathode pipe. Vacuum evacuation of the source may be accomplished through vacuum pumping through a pinch-off tube or valve attached to the source, or the assembly may be sealed in vacuum. The assembly is preferably heated during assembly to drive off residual gasses before being sealed to external atmosphere. This heating may be provided by a conventional or vacuum oven.

Internal support spacers such as shown in FIG. 2 may be made of glass, quartz, ceramic or other insulating materials, coated with a charge bleed layer. They are spaced depending on the thickness of the thinnest of the cathode or anode pipes. With a 2 mm thickness of borosilicate glass or quartz, for example, support structures should be provided at least every 200 mm.

In an alternative source of the present invention, a layer of material, such as MgO, with a high secondary electron emission coefficient is deposited on inner surface of the cathode pipe. Electrons from the cathode array(s) induce an amplified level of secondary electron emission, this beam current then being accelerated to the anode pipe.

The phosphors on the anode pipe may also be formed in discrete, electrically addressable sections, so that different phosphors may be selectively addressed for emission in different UV spectral bands. Address lines may be formed above or below the phosphor regions and used to provide the anode potential only at the addressed section.

The present invention is well adapted to carry out the objects and attain the ends and advantages described as well as others inherent therein. While the present embodiments of the invention have been given for the purpose of disclosure numerous changes or alterations in the details of construction and steps of the method will be apparent to those skilled in the art and which are encompassed within the spirit and scope of the invention.

What is claimed is:

1. A cathodoluminescent UV pipe source of ultraviolet light flux comprising:
   an inner pipe made of UV transmissive material and coated on its outer surface with a layer of cathodoluminescent UV emitting phosphor, said phosphor layer being covered with a thin layer of conductive, UV reflective material;
   an outer pipe with one or more cathode arrays disposed on or near its inner surface, and;
   end plates or flanges providing a vacuum hermetic seal of the space between the inner and outer pipes;
   the space between the inner and outer pipes being evacuated to a vacuum of at least 10−3 Torr, and;
   the cathode arrays operable to emit current which is accelerated across the vacuum space between the inner and outer pipes by an anode voltage to strike the UV phosphors which then emit UV flux which illuminates the inside of the pipe and material flowing through the inner pipe.

2. The pipe source of claim 1 in which UV-C phosphors belong to the group consisting of zirconium pyrophosphate; hafnium pyrophosphate; yttrium tantalate and lanthanum pyrophosphate.

3. The pipe source of claim 1 in which UV-C phosphors are operable as powder laser phosphors in response to pulsing of the electron beam current.

* * * * *